(12) United States Patent
Sintay et al.

(10) Patent No.: US 12,063,992 B2
(45) Date of Patent: Aug. 20, 2024

(54) METHOD OF CLOTHED TREATMENT DURING RADIATION THERAPY

(71) Applicant: The Moses H. Cone Memorial Hospital Operating Corporation, Greensboro, NC (US)

(72) Inventors: Benjamin Jeremiah Sintay, Summerfield, NC (US); Sudhakar Puvvada, Cary, NC (US); Thomas Lane Hayes, Greensboro, NC (US); David Brian Wiant, Kernersville, NC (US); Nicholas Corey Koch, Greensboro, NC (US)

(73) Assignee: The Moses H. Cone Memorial Hospital Operating Corporation, Greensboro, NC (US)

(*) Notice: Subject to any disclaimer, the term of this patent is extended or adjusted under 35 U.S.C. 154(b) by 0 days.

(21) Appl. No.: 18/305,422

(22) Filed: Apr. 24, 2023

(65) Prior Publication Data
US 2023/0255281 A1    Aug. 17, 2023

Related U.S. Application Data

(62) Division of application No. 17/097,922, filed on Nov. 13, 2020.

(60) Provisional application No. 62/935,998, filed on Nov. 15, 2019.

(51) Int. Cl.
| A61B 6/03 | (2006.01) |
| A41D 13/12 | (2006.01) |
| A61B 6/10 | (2006.01) |
| A61N 5/10 | (2006.01) |

(52) U.S. Cl.
CPC .......... A41D 13/1236 (2013.01); A61B 6/032 (2013.01); A61B 6/107 (2013.01); A61N 5/1077 (2013.01); *A61N 2005/1094* (2013.01)

(58) Field of Classification Search
CPC .... A41D 13/1236; A61B 6/032; A61B 6/107; A61N 2005/1094; A61N 2005/1096; A61N 5/1077
See application file for complete search history.

(56) References Cited

U.S. PATENT DOCUMENTS

2013/0019874 A1* 1/2013 Thompson ......... A41D 13/1254
128/845

* cited by examiner

*Primary Examiner* — Mark D Remaly
(74) *Attorney, Agent, or Firm* — Fox Rothschild LLP

(57) ABSTRACT

The presently disclosed subject matter relates generally to a treatment garment for use in clothed radiation treatment and diagnosis procedures, and methods of using the garment.

6 Claims, 3 Drawing Sheets

METHOD OF CLOTHED TREATMENT DURING RADIATION THERAPY

TECHNICAL FIELD

The present invention generally relates to a treatment garment for use in clothed radiation treatment and diagnosis procedures, and methods of using the garment.

BACKGROUND

There were an estimated 18 million new cancer cases around the world in 2018, of which an estimated 1.7 M cases were diagnosed in the United States. The most common cancers are in thoracic regions (breast, lung) and abdomen and pelvic regions (prostate, colon and rectum). Radiation therapy is often indicated for dozens of types of cancers. The radiation is intended to kill tumor cells and spare healthy surrounding tissue. Radiation therapy uses volumetric imaging, such as computed tomography (CT) scans, to both identify volumes of interest and create radiation treatment plans that deliver a maximal dose to the intended target and minimal radiation to the surrounding tissue.

Multiple radiation treatment sessions, typically ranging from a few days to 7 weeks, are utilized to deliver the required radiation necessary to kill the tumor, while sparing healthy tissue. It is particularly important that during each treatment session, the radiation is delivered to the affected tissue precisely and in a reproducible fashion. In particular, the radiation must be delivered to the same planned volume of tissue, the "target," each session. A reproducible set-up is necessary to ensure that the target site receives the intended cumulative dose of radiation, while sparing surrounding healthy tissue. Historically this involved placing permanent tattoos on the patient's skin, to enable precise set-up via laser triangulation. Surface imaging guided setup, which involves projecting a light field on the surface of the patient's skin to create a spatially accurate map of the patient's surface, has recently been used to complement tattoo-based setup. In each session, the surface map is compared to a reference surface from the treatment plan, to precisely adjust the shape and posture of the patient, and to accurately position the patient relative to the treatment machine. Dark skinned patients pose a specific challenge for surface guided alignment, since surface features and marks are not easily visualized by the cameras. This may create a racial disparity in the application of surface guided imaging, increases the time required to treat patients, and may reduce the accuracy of the setup. Thus, it would be desirable to provide an improved method for visualizing surface features and marks on the patient's skin, especially those with dark skin.

The curvatures, folds and irregularities surrounding the breast, the armpit, the perineum, scrotum, and labia can make it difficult to control radiation to these areas, and often leads to a higher than normal radiation dose in these regions. These high radiation doses can damage the affected skin during and after treatment sessions. Sweat and rubbing of the irradiated skin due to normal movement and by daily clothing further aggravate the problem. The resulting skin reaction may initially manifest itself as a slight erythema limited to small areas. As treatment progresses, reddening as well as inflammation tends to increase. Dry and moist desquamation can also develop in certain high dose regions and in areas where tissue folds upon itself.

To undergo radiation treatment, patients must typically partially or fully disrobe, so that radiation treatment can be delivered to uncovered regions of the skin, and positioning skin marks or tattoos can be easily visible. Irradiating the bare skin also prevents foreign objects, such as clothing, from increasing the radiation dose to the skin, or attenuating the treatment beam. The need to disrobe is disadvantageous to the patient, as cool temperatures in the treatment room can lead to discomfort. Further, the exposed patient is unable to protect their modesty, which can lead to a sense of vulnerability and loss in self-confidence, which is undesirable, as emotional distress can have a negative impact on treatment outcome. Thus, it would be desirable to provide a garment that can be worn by the patient during radiation, that does not interfere with the treatment.

SUMMARY

The present disclosure provides a garment for use by patients during radiation treatment and diagnostic procedures.

A first aspect of the disclosure provides a treatment garment for use by patients during radiation treatment and diagnostic procedures, including a fabric, wherein the garment is configured for wearing on at least a portion of a subject's body, to produce an increase in one ply local bolus effect factor ($\beta$) targeted to the subject's body of no more than 1.3 when the body is exposed, through the fabric, to a radiation beam having a polyenergetic x-ray energy of from 6 MV to 18 MV, or an electron beam having a nominal electron energy of from 6 MeV to 22 MeV. In some embodiments, the garment induces less than 5% change in percent depth dose at a depth of 10 cm in water for a 10-cm square field of the polyenergetic x-ray beam, which has a percent depth dose of greater than 60% at a depth of 10 cm in water at a 100 cm source-to-surface distance. In some embodiments, a 10-cm square field of the particle beam has a range of greater than 2 cm in water to the distal 50% fall-off of maximum dose, and the treatment garment induces a change of less than 2 mm in water to the distal 50% fall off of the particle beam. In some embodiments, the fabric has a drape coefficient of no more than 25%. In some embodiments, the garment has a color selected to optimize reflectance in the light field used for alignment. In some embodiments, the garment has a reflectance of from 25% to 100% at a wavelength of from 380 to 740 nm. In some embodiments, the garment has a color defined in CIELAB color space with an L* value greater than 25. In some embodiments, the fabric is selected from the group consisting of cotton, nylon, polyester, spandex, silk, linen, rayon or a combination thereof. In some embodiments, the garment is configured for wearing on at least a portion of at least one of an upper torso or a lower torso of a user's body. In some embodiments, the garment is selected from the group consisting of a shirt, dress or pants. In some embodiments, the garment is a sheet that is configured for laying on top of at least one of the upper or lower torso of the subject. In some embodiments, the garment is configured for wearing on at least a portion of the upper torso of a user, and is of a type selected from the group consisting of a shirt, camisole, sleeveless shirt, short sleeved shirt, long sleeved shirt, gown, or dress. In some embodiments, the garment is configured for wearing on at least a portion of the upper torso of a user, and comprises a neck border defining a neck insertion opening, and a pair of sleeve borders defining a pair of arm insertion openings. In some embodiments, the garment is configured for wearing on at least a portion of the upper torso of a user, and comprises an access flap in a rear portion of the garment. In some embodiments, the access flap is oriented vertically on the user's body. In some embodiments, the garment is configured for wearing on at least a portion of the lower torso of a user, and is of a type selected from the group consisting of shorts, cropped pants, or long pants. In some embodiments, the garment has at least one of a cutout or a visually transparent panel. In some embodiments, the garment is configured to be loose-fitting on the user's body.

A second aspect of the disclosure provides a method of treating a subject, including: providing to a subject a treatment garment according to the first aspect; aligning the subject wearing the garment, and positioning the garment on the subject, according to a reference geometry; and performing a radiation treatment on the subject. In some embodiments, the reference geometry is visually exhibited using at least one of surface imaging, or laser in combination with at least one body tattoo. In some embodiments, the method further includes selecting the garment based on the subject's size.

A second aspect of the disclosure provides a method of providing a consistent surface for surface imaging during treatment, including: providing to a subject a treatment garment according to the first aspect; aligning the subject wearing the garment, and positioning the garment on the subject, according to a reference geometry; and performing a radiation treatment on the subject.

A second aspect of the disclosure provides a method of conducting a diagnostic procedure including exposing a subject to radiation, wherein the subject is wearing a treatment garment according to the first aspect.

DETAILED DESCRIPTION

Figure 1:
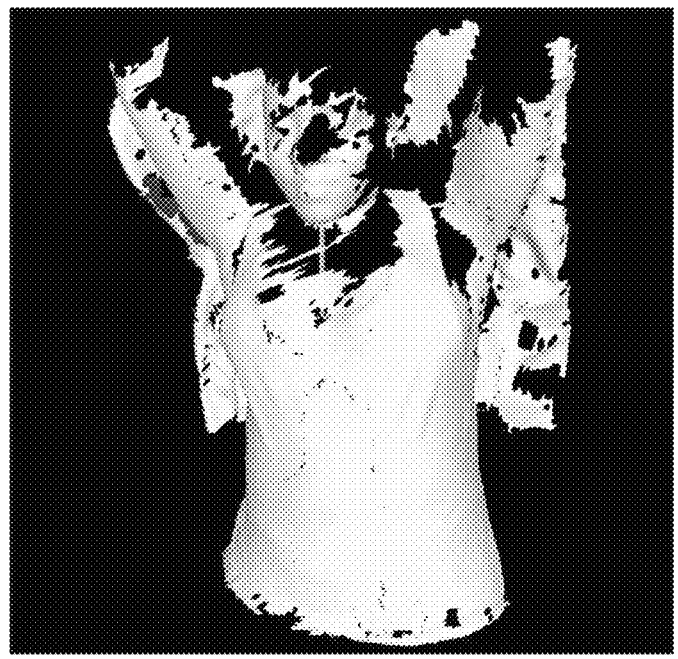
FIG. 1 illustrates a front view of a dark-skinned patient wearing the treatment garment while being scanned by an Align RT® surface guided imaging system.

The presently disclosed subject matter, which will now be described more fully, can be embodied in different forms and should not be construed as limited to the embodiments set forth herein. The following detailed description is exemplary in nature and is not intended to limit the scope, applicability, or configuration of the disclosure in any way. Rather, the following description provides some practical illustrations for implementing examples of the present disclosure. Examples of constructions, materials, dimensions, and manufacturing processes are provided for selected elements, and all other elements employ that which is known to those of ordinary skill in the field of the disclosure. Those skilled in the art will recognize that many of the noted examples have a variety of suitable alternatives.

The treatment garment disclosed herein is suitable for wearing by a subject during at least one of radiation treatments, radiation diagnostic procedures, or radiation planning sessions. The treatment garment provides at least one of the following advantages: treating patients with radiation therapy while they are clothed; providing dignity of the patient while undergoing treatment; reducing patient emotional distress or anxiety amongst patients; providing the patient warmth and comfort in the treatment room; providing a consistent surface for alignment and surface imaging; providing improved alignment of patients using at least one of skin marks or tattoos, or surface imaging techniques; improving visibility and alignment of darker skin patients; providing additional means to position the subject's anatomy; or providing absorption for incontinent patients.

When foreign objects are placed in the path of a radiation beam, the energy deposition is perturbed. The degree of perturbation depends on the linear mass density of the foreign object or perturbing material, and its distance from the radiation beam. The perturbation reaches a maximum behind the perturbing material, immediately distal to the source of the radiation beam, which can result in an increase or decrease in energy deposition. During radiation treatment or radiation diagnosis procedures, the body of the patient experiences an increase in radiation energy deposition. When the patient is clothed, the clothing on the patient's body serves as a foreign object or perturbing material that undesirably causes a further increase in radiation energy deposition, the surface "bolus effect." This bolus effect can lead to skin toxicity and irritation, and in some cases, even burning or death. Therapeutic radiation beams, from x-ray and electron beams, generally exhibit a skin-paring effect that is spoiled by the perturbing material. The beam spoiling is manifested as a local increase in the energy deposited by a megavoltage radiation beam at depths more shallow than the beam's depth of maximum dose. In the presence of a foreign or perturbing object, it is not possible to stop the bolus effect completely, however it was unexpectedly discovered that it is possible to limit the bolus effect caused by the clothing, by using the disclosed treatment garment.

The disclosed treatment garment can be worn for use with any radiation treatment or diagnosis machine, without causing a substantially increased bolus effect. In some embodiments, the garment is configured for wearing on at least a portion of a subject's body, to produce a local bolus effect factor of no more than 1.3 when the body is exposed, through the fabric, to a polyenergetic x-ray radiation beam or a therapeutic particle beam. In some embodiments, the local bolus effect factor, β, increase in radiation is a one-ply bolus effect increase, or the increase in radiation energy deposition caused by the presence of a single ply of the fabric on the subject's body. In some embodiments, the treatment garment on the clothed subject produces a local bolus effect factor, β, of no more than 1.3 when the body is exposed, through the fabric, to a radiation beam. In some embodiments, the treatment garment produces a local bolus effect factor increase in radiation dosage targeted to a user's body of no more than 1.25, no more than 1.2, no more than 1.15, no more than 1.1, or no more than 1.05. By "local bolus effect factor, β" is meant the ratio of the radiation dose or ionization charge readings with fabric over that without fabric at a shallow depth. Therefore, β equal to 1.0 indicates no perturbation by the material at the depth in question. Similarly, β equal to 1.3 indicates a 30% increase. In some embodiments, the bolus effect factor is a one-ply local bolus effect factor, or the bolus effect factor caused by a one-ply fabric. In some embodiments, the polyenergetic x-ray has an energy of from 6 MV to 18 MV. In some embodiments, the therapeutic particle beam has a range in water to the distal 50% of 2 cm or greater. In some embodiments, the garment is configured for wearing on at least a portion of a subject's body, to produce a local bolus effect factor of no more than 1.3 when the body is exposed, through the fabric, to a polyenergetic x-ray radiation beam of 6 MV up to 18 MV, or a therapeutic particle beam with a range in water to the distal 50% of 2 cm or greater As noted above, the treatment garment can be worn when the subject is undergoing treatment or diagnosis using any suitable radiation treatment or diagnosis machine, such as for example an x-ray, computerized tomography (CT) scan, or magnetic resonance imaging (MRI) machine. The treatment garment is suitable for use in treatment or diagnosis procedure using radiation energy that is high enough that the garment does not hinder the effectiveness of the procedure. Radiation therapy uses high-energy particles or waves, such as x-rays, gamma rays, electron beams, or protons, to destroy or damage cancer cells. In some embodiments, the treatment garment produces a bolus effect increase in a radiation dosage targeted to a user's body of no more than 30% when exposed to a polyenergetic x-ray having an energy of from 6 MV to 18 MV. In some embodiments, the treatment garment produces a local bolus effect factor increase in a radiation dosage targeted to a user's body of no more than 25%, no more than 20%, no more than 15%, no more than 10%, or no more than 5%, when exposed to a polyenergetic x-ray having an energy of from 6 MV to 18 MV. In some embodiments, a transversal of the treatment garment induces less than a 5% change in percent depth dose at a depth of 10 cm for a 10-cm square field of the polyenergetic x-ray beam, which has a percent depth dose of greater than 60% at a depth of 10 cm in water at 100 cm source-to-surface distance. In some embodiments, the treatment garment produces a local bolus effect factor increase in a radiation dosage targeted to a user's body of no more than 1.3 with 1 ply of fabric versus no fabric. In some embodiments, the treatment garment induces a change in beam range, i.e., depth in water to the distal 50% fall off point, of no more than 2 mm when exposed to a therapeutic particle beam having a range of 2 cm or greater, including an electron beam having a nominal electron energy from 6 MeV to 22 MeV. By "nominal electron energy" is meant the beam energy label assigned and specified by the manufacturer of the radiation producing equipment, or the beam energy defined by the range in water to the distal 50% of maximum dose under standard reference conditions recommended in the report of Task Group 51 of the American Association of Physicists in Medicine. In some embodiments, the treatment garment produces a local bolus effect factor increase in a radiation dosage targeted to a user's body of no more than 1.25, no more than 1.2, no more than 1.15, no more than 1.10, or no more than 1.05, when exposed to an electron beam having a nominal electron energy of from 6 MeV to 22 MeV. In some embodiments, the electron beam has a range of 2 cm or greater in water to the distal 50% fall-off of maximum dose at 100 cm source-to-surface distance. By "the distal 50% fall-off of maximum dose" is meant the point along the radiation depth dose profile, under standard reference conditions recommended in the report of Task Group 51 of the American Association of Physicists in Medicine, where the dose decreases to 50% of the maximum dose.

Any suitable fabric that is capable of being worn during a radiation treatment or diagnosis, without causing the increased bolus effect, as described above, can be used. In some embodiments, the garment has a density of no more than about 200 g/m$^2$. In some embodiments, the garment has a density of no more than 175 g/m$^2$, no more than 150 g/m$^2$, no more than 125 g/m$^2$, no more than 115 g/m$^2$, no more than 100 g/m$^2$, no more than 90 g/m$^2$, or no more than 80 g/m$^2$. In some embodiments, the garment has a density of from about 60 g/m$^2$ to about 100 g/m$^2$. In some embodiments, the garment has a density of from about 70 g/m$^2$ to about 90 g/m$^2$. In some the garment has a density of about 80 g/m$^2$.

In some embodiments, the garment is substantially undetectable during CT scan and water phantom dosimetry testing.

As noted above, the radiation must be delivered to the same planned volume of tissue, the "target," during each session, while sparing surrounding healthy tissue. To facilitate this, the treatment garment is made of a fabric that has sufficiently high drape that the garment can substantially conform to the shape of the body on which it is worn. In some embodiments, the fabric has a drape coefficient (F) of no more than 25%, as measured using the Cusick drape meter. In some embodiments, the fabric has a drape coefficient of no more than 20%, no more than 15%, or no more than 10%, as measured using the Cusick drape meter. The drape coefficient (F) has been developed to measure the degree of drape and is measured using the Cusick drape meter. The Cusick drape meter uses a parallel beam of light to cast a shadow from a circular piece of fabric supported by a smaller circular disk. The area of the shadow (As) is measured and compared with the area of the sample (Af) and that of the supporting platform (Ap). The drape coefficient F is defined as:

$$F = \frac{(A_s - A_p)}{(A_f - A_p)} \times 100\%$$

where F ranges from 0 to 100%.

The fabric may be made of one type of material, or it can be a blend of different materials. In some embodiments, the fabric is selected from at least one one of cotton, nylon, polyester, spandex, silk, linen, or rayon. In some embodiments, the fabric is a woven, non-woven, or knit fabric. In some embodiments, the treatment garment includes at least one design feature, such as for example, a print or pattern. In some embodiments, the garment includes at least one design feature that is configured to improve patient alignment. The fabric may have any suitable thickness, ranging from thin to thick, as long as it does not significantly attenuate radiation at the target site. In some embodiments, the fabric has at least one of antimicrobial properties, moisture wicking properties, provides a cooling sensation on the skin, or not irritating to the skin, or does not exacerbate irritated skin.

As described above, surface guided imaging is often used to create a reproducible setup, ensuring that the target site receives the intended cumulative dose of radiation, while sparing surrounding healthy tissue. Surface guided imaging operates by capturing light reflected from the patient. Consequently, this surface guided imaging is challenging when treating dark-skinned subjects. To account for differences in skin color, the radiation system aperture typically needs to be changed manually, adjusting for the patient's unique skin color. The system's geometric calibration would ideally be adjusted due to different light penetration. This disadvantageously adds time to the overall treatment or diagnostic procedure. The treatment garment enables the surface guided imaging to be performed without necessitating the adjustments for skin color, which saves time. FIG. 1 shows a dark-skinned patient wearing the treatment garment while being scanned by an Align RT® surface guided imaging system. Although the system is unable to visualize the individual's skin features, it easily visualizes the garment on the body, and thus improves alignment. This enables a reproducible procedure set-up, and hence the delivery of radiation to the same target tissue during each session, while also saving time.

The treatment garment fabric can have any suitable color that does not interfere with effective functioning of surface guided imaging. The color of the garment has an impact on the absorption of different wavelengths of light emitting from the surface guided imaging system. Garments having certain colors, such as for example, dark colors like black, brown and dark blue, will disadvantageously absorb certain wavelengths, leading to poor visibility of the surface guided imaging light. The treatment garment color is selected so that it will effectively reflect the wavelength of light generated by the surface imaging system. Thus, the garment color is compatible with surface guided imaging system wavelengths. In some embodiments, the treatment garment has a light color. In some embodiments, the treatment garment has a color, as defined by the International Commission on Illumination (CIE) L*a*b* (CIELAB) color scale, having an L* value of greater than 25. The CIELAB color space expresses color as three values, namely "L*" for the lightness ranging from black (0) to white (100); "a*" from green (−) to red (+), and "b*" from blue (−) to yellow (+). An L* value of 100 represents a perfect reflecting diffuser. In some embodiments, the treatment garment has a color, as defined by the International Commission on Illumination (CIE) L*a*b* (CIELAB) color scale, having an L* value of greater than 30, greater than 35, or greater than 45. In some embodiments, the treatment garment has a color selected from white, off-white, beige, shades of green, such as for example, emerald, mint, turquoise, and sea green; shades of blue, such as for example, azure, neon blue, royal blue, violet blue, and sky blue; or shades of purple, such as for example, lilac, lavender, purple, violet, indigo, and grape.

The treatment garment fabric should have a sufficiently low shine so as to not negatively impact the functioning of surface guided imaging system. If the gloss of the fabric is too high, this can cause a partial or full loss of the imaging signal, making it difficult to properly align the subject. In some embodiments, the treatment garment has a reflectance of from 25% to 100% at a wavelength of from 380 to 740.

The treatment garment is designed and constructed to support patients and aid physicians and therapists in their treatment. The garment provides adequate coverage of body regions, such as for example breasts, nipples, crotches, pubic areas, stomach, and buttocks, providing patient modesty, while also ensuring access and visibility to physicians and therapists of radiation marks and other body features to facilitate treatment. Subjects receiving surgical interventions for their cancer may be sore, and the surgeries may restrict movements of certain body parts. As a result, the garment is constructed in a manner that allows subjects to easily put on and take off the garment. The garment can also be configured so as to cover the body adequately to provide warmth in the often-cold procedure rooms.

The treatment garment is configured for wearing on the body of a subject. The treatment garment may be suitable for wearing on the upper torso or lower torso of the subject, or both. In some embodiments, the garment is a sheet that is configured for laying on top of at least one of the upper or lower torso of the subject. In some embodiments, the garment is a shirt, a dress or a pair of pants. In some cases, the garment is a shirt, camisole, sleeveless shirt, short sleeved shirt, long sleeved shirt, gown, or dress. In some cases, the garment is a pair of underwear, shorts, athletic shorts, cropped pants, or long pants. The treatment garment has strategically placed insertion openings through which the subject can insert various body parts. In some embodiments, the garment has at least one cutout. In some embodiments, the garment has at least one visually transparent panel. The insertion openings, cutouts and transparent panels can be used, for example, to enable the practitioner to view tattoos or radiation marks on the subject's body which are used to guide alignment of the subject. The size and location of the insertion openings, cutouts or transparent panels can be selected based, for example, on the type of cancer, location of cancerous cells, or the subject's body dimensions.

The garment can have any suitable fit on the subject's body. In some embodiments, the garment is configured to be loose-fitting on the user's body. By loose-fitting is meant that the garment does not follow the contours of the body being covered and is easy to put on and take off.

In some embodiments, the garment has a belt-like tie that can be used to tighten the garment. This can help to ensure that the garment is positioned consistently and prevent bunching up on the sides. In some embodiments, the garment also includes at least one belt loop on one or both sides of the garment, through which the belt-like tie can be placed.

Figure 2:
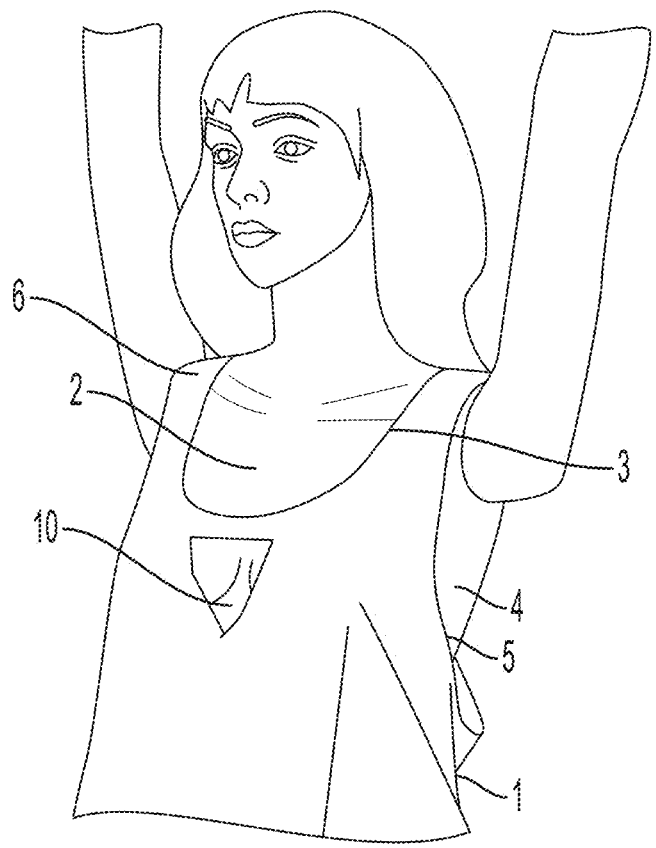
FIG. 2 illustrates an angled front view of a subject wearing a treatment garment having a cutout.
Figure 3:
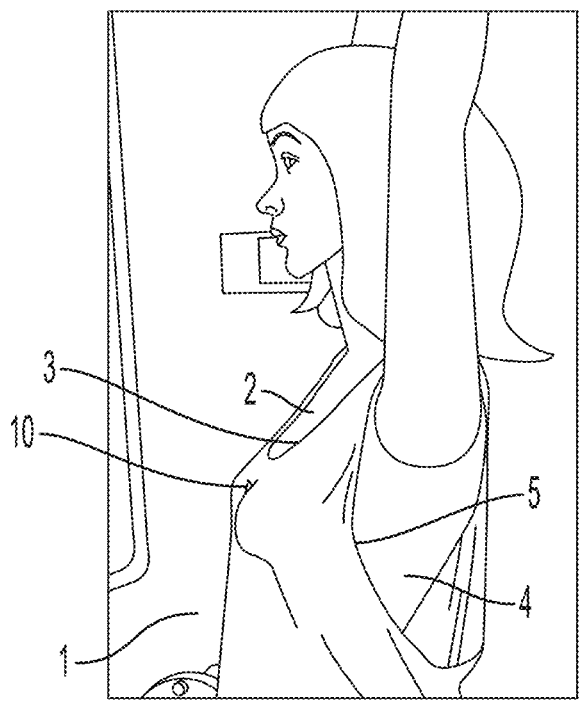
FIG. 3 illustrates a side view of a subject wearing a treatment garment
Figure 4:
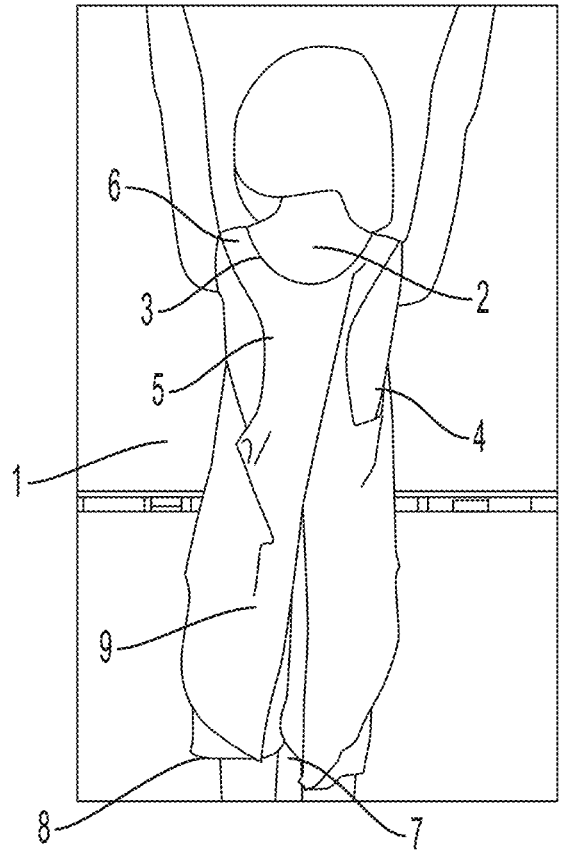
FIG. 4 illustrates a rear view of a subject wearing a treatment garment having an access flap.

FIGS. 2 to 4 show an embodiment the treatment garment from various angles. The garment 1 is configured for wearing on at least a portion of the upper torso and lower torso of a subject. The garment 1 has strategically placed open portions through which the subject can insert their head, neck and arms. The neck insertion opening 2 is bordered by a neck border 3 that defines the neck insertion opening 2. The two arm insertion openings 4 are each bordered by a sleeve border 5 that defines the arm insertion opening 4. The neck insertion opening 2 is sufficiently large to enable the subject to easily place their head and neck through the neck insertion opening 2, and rest the sleeves 6 of the garment 1 on their shoulders. The arm insertion openings 4 are sufficiently large to enable the subject to easily place their arms through the arm insertion openings 4. The lower portion of the garment 1 is draped around the legs of the subject. The leg insertion opening 7 at the bottom of the garment 1 is defined by a leg opening border 8. The rear portion (FIG. 4) of the garment 1 has an access flap 9 that facilitates ease of putting on the garment 1, and allows easy access to the subject's body, while concealing the back portion of the subject's body. The access flap 9 is oriented substantially vertically on the subject's body, although it can have a different orientation. The garment 1 has a cutout 10 between the breast region, along the sternum. The cutout 10, as well as the large arm insertion openings 4 help the practitioner to visualize any tattoo marks on the subject's body.

The present disclosure also provides methods of using the treatment garment. Some embodiments provide at least one of a method of providing a consistent surface for surface imaging during treatment, or a method of treating a subject. In some cases, the garment is selected based on at least one of the patient's size, type of cancer, or location of cancerous cells. The subject who is wearing the treatment garment is aligned on a surface in preparation for treatment. The garment is positioned on the subject according to a reference geometry. Any suitable reference geometry system can be used. In some cases, the reference geometry system is a visible light beam emitted from a surface imaging system. In some cases, the visible light beam is a laser beam. In some cases, the reference geometry system aligns the light beam with a temporary ink or permanent ink (tattoo) marking on the patient's skin to align the treatment area within the patient's body with the radiation beam to be applied to the body. The radiation treatment is then performed on the properly aligned subject.

Additionally, the present disclosure also provides a method of conducting a diagnostic procedure by exposing a subject who is wearing a treatment garment to radiation.

While different embodiments of a treatment garment are described, skilled artisans will understand that any of the features of one embodiment can be incorporated into the other embodiments. Any combination of the features described in any of the embodiments can be included in the treatment garment and are within the scope of the invention.

It will be understood that various details of the presently disclosed subject matter may be changed without departing from the scope of the presently disclosed subject matter. Furthermore, the foregoing description is for the purpose of illustration only, and not for the purpose of limitation.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1—Fabric Development—Surface Bolus Effect

Several fabrics were evaluated for their effect on energy deposition at shallow depths. Variables tested included (a) range of materials spanning across cotton, nylon, polyester and spandex, (b) fabric density, (c) different thicknesses and openness, (d) different constructions ranging from knit fabrics, woven fabrics and non-woven fabrics, and (e) shine/gloss. All fabrics tested were white or off white in color.

This study was conducted using a 6 MV photon beam on a TrueBeam linear accelerator (Varian Medical Systems, Palo Alto, CA). A slab phantom consisting of water equivalent material was placed, with the surface of the phantom at a source to surface distance of 100 cm from the linear accelerator. A parallel plate ionization chamber was placed at a depth of 0.5 mm below the surface. Measurements were made with no fabric present, 1 ply, and 4 ply layers of fabric. The measurements with fabric were compared to the measurements without fabric to evaluate surface dose increase resulting from the fabric.

The results at a shallow depth should have shown negligible dose impact due to the fabric. As shown in Table 1 below, the results at the surface unexpectedly revealed that most fabrics have a significant impact on radiation. In many fabrics, the increase can lead to radiation burns. To minimize skin toxicity, it is important to select a fabric which limits the local bolus effect.

TABLE 1

| Local Bolus Effect Factors, $\beta$ | | | | |
|---|---|---|---|---|
| Fabric | | | $\beta$ | |
| Code | Sample | Density | 4 Ply | 1 Ply |
| A1 | Very Light Weight Non-woven (CO102) | 35.0 | 1.08 | 1.02 |

TABLE 1-continued

| Local Bolus Effect Factors, $\beta$ | | | | |
|---|---|---|---|---|
| Fabric | | | $\beta$ | |
| Code | Sample | Density | 4 Ply | 1 Ply |
| B2 | Mid Weight Stretch Nonwoven | 214.6 | 1.38 | 1.12 |
| A6 | 100% Cotton Flannel | 197.2 | 1.39 | 1.11 |
| F9 | Polyester Spandex | 87.8 | 1.18 | 1.05 |
| K1 | Nylon Spandex | 167.5 | 1.36 | 1.10 |
| K3 | Nylon Spandex - Mesh | 85.8 | 1.19 | 1.05 |
| L2 | Cotton Spandex | 280.3 | 1.51 | 1.15 |
| AR1 | Polyester Cotton Spandex | 214.4 | 1.39 | 1.11 |
| B3 | Light weight Stretch Non-woven | 154.3 | | 1.09 |
| K7 | Polyester Spandex | 205.6 | | 1.12 |
| K6 | Cotton Spandex | 197.0 | | 1.12 |
| K10 | Polyester Spandex (14%) | 227.1 | | 1.14 |
| L1 | Cotton Spandex | 116.6 | | 1.07 |

Figure 5:
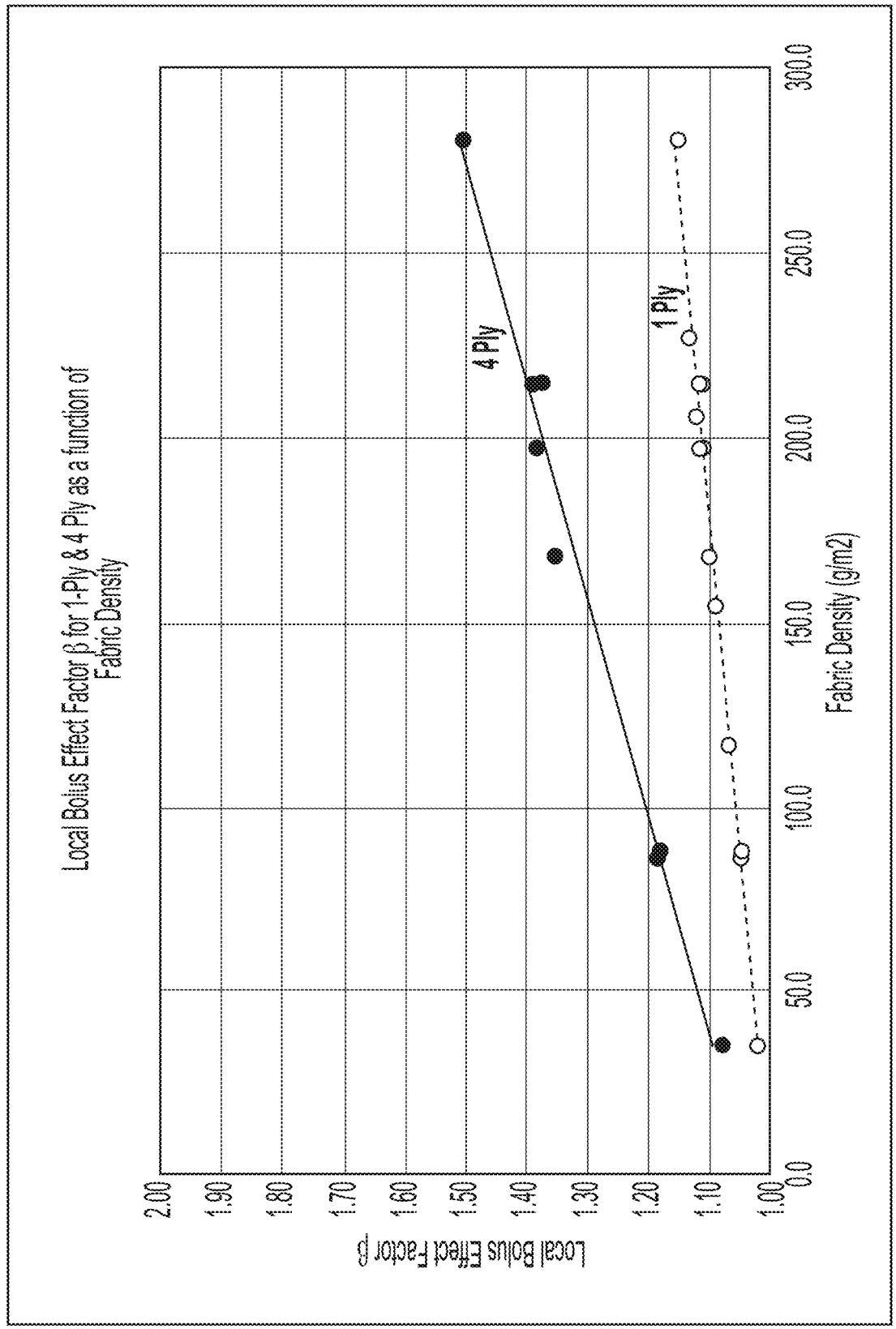
FIG. 5 illustrates a chart of local bolus effect factor, β, for different fabric densities for 1 ply and 4 ply fabric thickness.

The effect of fabric thickness on the intensity increase (bolus effect) was also assessed. FIG. 5 illustrates a chart of local bolus effect factor, $\beta$, for different fabric densities for 1 ply and 4 ply fabric thickness.

Example 2—Visibility of Dark Skin Patients

FIG. 1 shows a dark-skinned patient wearing a treatment garment being scanned by an Align RT® surface guided imaging system. Although the system was unable to visualize the individual's skin features, it did easily visualize the garment on the body, and thus improved alignment.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method of treating a subject, comprising:
   a. providing to a subject a loose-fitting treatment garment that is configured to be worn on at least a portion of the subject's body to produce a local bolus effect factor of no more than 1.3 when the body is exposed, through the fabric, to a polyenergetic x-ray radiation beam of from 6 MV up to 18 MV, or a therapeutic particle beam with a range in water to the distal 50% of 2 cm or greater;
   b. aligning the subject wearing the garment, and positioning the garment on the subject, according to a reference geometry, the positioned garment being loose-fitting on the portion of the subject's body; and
   c. performing a radiation treatment on the subject.

2. The method according to claim 1, wherein the reference geometry is visually exhibited using at least one of surface imaging, or laser in combination with at least one body tattoo or ink marking.

3. The method according to claim 1, wherein the method further includes selecting the garment based on the subject's size.

4. The method of claim 1, wherein the positioned garment is loose-fitting on the portion of the subject's body such that the garment does not follow one or more contours of the portion of the subject's body covered by the garment.

5. A method of providing a consistent surface for surface imaging during treatment, comprising:
   a. providing to a subject a loose-fitting treatment garment wherein the garment is configured for wearing on at least a portion of a subject's body, to produce a local bolus effect factor of no more than 1.3 when the body is exposed, through the fabric, to a polyenergetic x-ray radiation beam of from 6 MV up to 18 MV, or a therapeutic particle beam with a range in water to the distal 50% of 2 cm or greater;

b. aligning the subject wearing the garment, and positioning the garment on the subject, according to a reference geometry, the positioned garment being loose-fitting on the portion of the subject's body; and c. performing a radiation treatment on the subject.

6. A method of conducting a diagnostic procedure comprising exposing a subject to radiation, wherein the subject is wearing a loose-fitting treatment garment on at least a portion of the subject's body to produce a local bolus effect factor of no more than 1.3 when the body is exposed, through the fabric, to a polyenergetic x-ray radiation beam of from 6 MV up to 18 MV, or a therapeutic particle beam with a range in water to the distal 50% of 2 cm or greater.

* * * * *